(12) United States Patent
Hubbard et al.

(10) Patent No.: US 7,210,898 B2
(45) Date of Patent: May 1, 2007

(54) GAS REMOVAL FROM A CENTRIFUGAL PUMP

(76) Inventors: Lloyd Hubbard, 20645 Bayview Ct., Deephaven, MN (US) 55331; Earl Clausen, 1670 Wild Ridge Ct. South, Newport, MN (US) 55055

( * ) Notice: Subject to any disclaimer, the term of this patent is extended or adjusted under 35 U.S.C. 154(b) by 154 days.

(21) Appl. No.: 10/966,657

(22) Filed: Oct. 15, 2004

(65) Prior Publication Data

US 2006/0084836 A1   Apr. 20, 2006

(51) Int. Cl.
*F04D 29/00* (2006.01)

(52) U.S. Cl. .............. 415/169.1; 415/115; 415/900
(58) Field of Classification Search .......... 415/169.1, 415/900, 115; 604/6.09, 6.11
See application file for complete search history.

(56) References Cited

U.S. PATENT DOCUMENTS

| | | | |
|---|---|---|---|
| 3,768,726 A * | 10/1973 | Hale et al. ............ | 494/10 |
| 4,157,965 A | 6/1979 | Raible | |
| 4,919,802 A * | 4/1990 | Katsura ............ | 422/44 |
| 5,770,149 A * | 6/1998 | Raible ............ | 422/46 |
| 5,957,880 A | 9/1999 | Igo et al. | |
| 6,337,049 B1 | 1/2002 | Tamari | |
| 6,432,136 B1 | 8/2002 | Weiss et al. | |
| 6,730,267 B2 | 5/2004 | Stringer et al. | |
| 6,773,670 B2 * | 8/2004 | Stringer et al. ........ | 422/44 |
| 2005/0192525 A1 * | 9/2005 | Wieting et al. ........ | 604/6.09 |

OTHER PUBLICATIONS

Morita, Masanori et al., Closed Circuit Cardiopulmonary Bypass with Centrifugal Pump for Open-Heart Surgery: New Trial for Air Removal, Artificial Organs, vol. 24, No. 6, 2000; pp. 442-445.

\* cited by examiner

*Primary Examiner*—Ninh H. Nguyen
(74) *Attorney, Agent, or Firm*—Kinney & Lange, P.A.

(57) ABSTRACT

A centrifugal pump includes a system that removes gas that accumulates along the axis of rotation of the shaft and/or impeller of the pump. One or more vent inlets are placed in the region where the gas accumulates and a suction device draws the accumulated gas through the vent inlets and a vent out of the centrifugal blood pump.

17 Claims, 7 Drawing Sheets

GAS REMOVAL FROM A CENTRIFUGAL PUMP

BACKGROUND OF THE INVENTION

The present invention relates to centrifugal blood pumps. In particular, the present invention relates to centrifugal blood pumps that remove accumulated gas.

Delicate surgical procedures require that the site of surgery remain motionless. This requirement made early heart surgery difficult as interrupting the heart's pumping action for the required length of time was invariably fatal.

Traditional heart surgery is carried out with the aid of a "heart/lung machine." With the heart/lung machine in operation, the patient's heart is stopped while the surgeon performs the delicate surgery required to repair the ailing heart. The two fundamental parts of the heart/lung machine are a blood pump that takes the place of the arrested heart, and an oxygenator that replaces the patient's lungs during the surgical procedure. The heart/lung machine also includes filters, blood reservoirs, and plastic tubing as required to connect the several parts of the bypass circuit.

Although the mortality and morbidity of heart/lung bypass surgery has been greatly reduced over the past several years, hospital stays of two weeks and gradual recoveries of over six months are common. Many of the bad side-effects of heart/lung bypass surgery are thought to result from prolonged blood contact with the various parts of the heart/lung machine.

A new technique for heart surgery has been developed and is generally referred to as "surgery on the beating heart." In this technique, a stabilizing device is commonly used to hold steady the portion of the heart that is being addressed by the surgeon. A heart/lung machine is not required, because the heart and lungs function normally throughout the procedure. The claimed advantages for this technique include reduced hospital stay, reduced hospital cost, and fewer side-effects such as mental deficit. It is claimed that all of these advantages are the result of reduced blood trauma by elimination of blood contact with the components of the heart/lung machine.

Beating-heart surgery is most commonly used for coronary artery bypass procedures. The procedure is not without problems both for the surgeon and the patient. First, the most commonly used stabilizing device consists in part of a series of small suction cups that grasp the portion of the heart being stabilized. The relatively high vacuum required to grasp the heart may result in blood blisters at the site of the suction cups. Second, since the heart is pumping and the coronary arteries filled with blood, the surgeon must contend with spurting from the coronary artery during the grafting procedure. Third, the cost of disposable devices is comparable to that required for conventional open-heart surgery;

The component of the heart/lung machine that is most suspect for causing blood trauma is the oxygenator. This is typically a device containing hundreds of hollow plastic fibers. During the heart/lung bypass surgery, the patient's blood passes over the outside surface of the fibers, while oxygen is passed through the fibers. Gas exchange imitates the function of natural lungs, but unlike the natural lungs, the oxygenator fibers are made from a plastic material and must have a large surface area in order to oxygenate the blood and to remove carbon dioxide from it.

Traditional heart/lung bypass procedures require placement of a cannula in the vessel (the vena cava) where oxygen-depleted blood is returned to the heart. Because the patient is on an operating table that is at a higher level than the heart/lung machine, a siphoning action draws the venous blood to the heart/lung machine. Air is routinely entrained with the blood, and if not removed, could have fatal consequences for the patient. Therefore, the blood/air mixture is typically directed to a reservoir where the air escapes into the operating room.

New designs for "minimal" heart/lung machines have been recently introduced. These minimal machines are typically "closed" circuits, placed at the level of the operating table to minimize the length of tubing required for the bypass circuit. Because the closed circuit has no inherent means of dealing with entrained air, a special "air removal" feature must be designed into the system. Typically, membrane filters are incorporated into the "minimal" circuit for this purpose. However, the pore size of these membranes is restricted to a diameter that will allow cellular elements of the blood to pass through. This requirement can compromise the membrane's ability to trap entrained air.

BRIEF SUMMARY OF THE INVENTION

Centrifugal pumps naturally tend to separate entrained gasses from the pumped fluid. Entrained gas typically concentrates in the center of the pump. The present invention is a centrifugal blood pump that removes gas, which accumulates within the pump. A vent inlet is positioned in a component of the centrifugal pump that is located along the axis of rotation. This is the area where gas accumulates within the pump housing. A vent communicates with the vent inlet at one end and suction tubing at the other end. Suction draws the gas through the vent inlet and vent, thus, removing the gas from the centrifugal pump.

DETAILED DESCRIPTION

Figure 1:
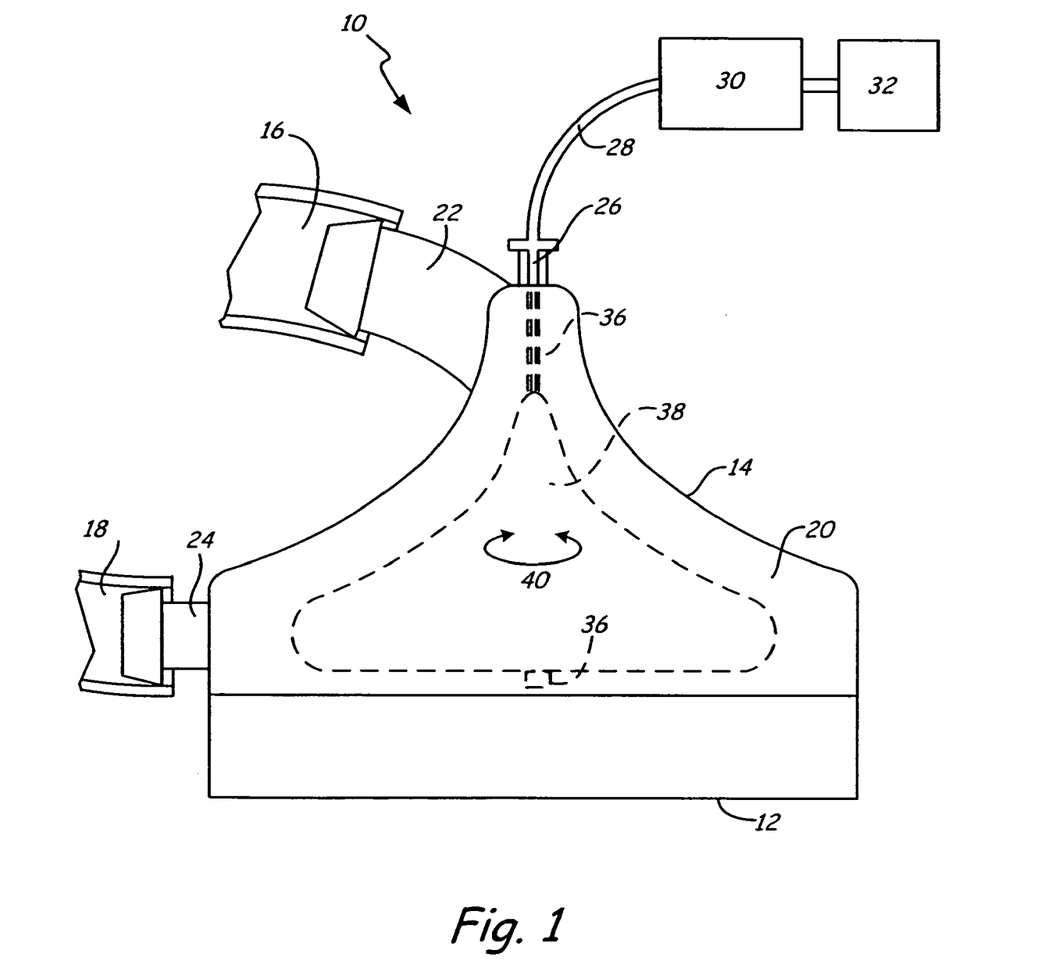
FIG. 1 is a front view of a centrifugal blood pump with a gas removal system.

FIG. 1 is a front view of an embodiment of the present invention. FIG. 1 shows pump system 10 with pump drive 12, centrifugal blood pump 14, inlet tubing 16, outlet tubing 18, reservoir 30, and suction device 32. Pump 14 includes housing 20, blood inlet 22, blood outlet 24, suction port 26, and suction tubing 28, shaft 36, impeller 38, and axis of rotation 40.

Pump drive 12 is coupled to pump 14. Inlet tubing 16 is in fluid communication with blood inlet 22, and outlet tubing 18 is in fluid communication with blood outlet 24. Inlet 22 and outlet 24 each extend from housing 20. Suction port 26 fluidly couples suction tubing 28 to pump 14 at one end. The opposite end of suction tubing 28 is in fluid communication with reservoir 30, which is in fluid communication with suction device 32.

In operation, pump system 10 is part of a heart bypass circuit or heart/lung machine. Pump drive 12 rotates impeller 38 of centrifugal blood pump 14, typically, through magnetic coupling. Blood enters pump housing 20 via tubing 16 and inlet 22. Blood is propelled by impeller 38 to and through outlet 24 and tubing 18.

During operation, gas entrained in the blood stream received at inlet 22 accumulates inside pump housing 20. The gas tends to accumulate along axis of rotation 40 of impeller 38 and shaft 36 coupled to impeller 38. Typically, it concentrates at a position where shaft 36 and/or impeller 38 have a minimum diameter. Suction device 32 draws the gas out of pump housing 20 via suction tubing 28 and reservoir 30. Reservoir 30 is typically a cardiometry reservoir. The mechanism for gas removal may be performed by any of number of ways. Embodiments are discussed in reference to FIGS. 2–7.

Figure 2:
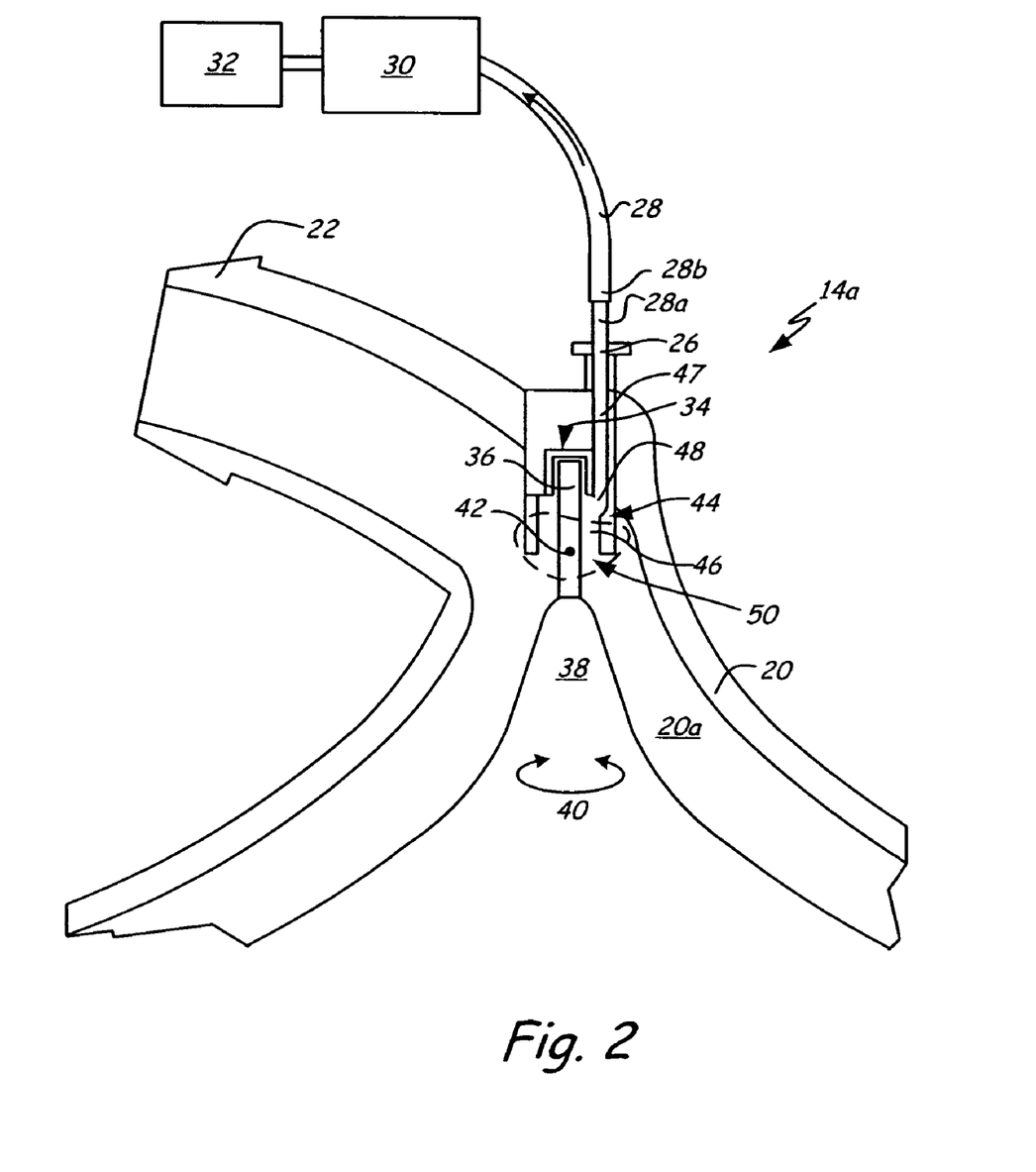
FIG. 2 is a cross-sectional view of a first embodiment of the present invention.

FIG. 2 is a first embodiment showing pump 14a. Pump 14a includes pump housing 20, pump chamber 20a, inlet 22, suction port 26, suction tubing 28 with sections 28a and 28b, bearing 34, rotating shaft 36, impeller 38, axis of rotation 40, sensor 42, shroud 44, collection space 46, vent 47, and vent inlet 48. FIG. 2 also shows reservoir 30, suction device 32, and accumulated gas 50.

Rotating shaft 36 is located along a midline within pump chamber 20a. Rotating shaft 36 is supported at its top end by bearing 34, and the bottom end of shaft 36 is connected to impeller 38. Shaft 36 and impeller 38 rotate around axis of rotation 40. Sensor 42 is shown located on shaft 36, however, it may be located on shroud 44 or any other structure that facilitates sensor 42 sensing the presence of gas in pump chamber 20a. Shroud 44 extends out from housing 20 and surrounds but does not contact shaft 36. Collection space 46 is formed between shaft 36 and shroud 44. Suction tubing 28 extends into housing 20 and may be from two or more sections of tubing. These may include flexible and inflexible tubing. Suction tubing 28, for example, is shown composed of two sections, section 28a and section 28b, coupled together. Vent 47 and vent inlet 48 allow fluid communication between collection space 46 and suction tubing 28. Vent 47 may be formed by any of a number of ways as will become apparent in the figures that follow.

In operation, blood flows into chamber 20a via inlet 22. Shaft 36 and impeller 38 rotate around axis of rotation 40 to propel the blood. During operation, accumulated gas 50 accumulates near and around shaft 36 along axis 40. As accumulated gas 50 accumulates, it is collected in collection space 46. Suction device 32 draws accumulated gas 50 through vent inlet 48, vent 47, and suction tubing 28 out of chamber 20a.

Suction device 32 may apply suction intermittently or continuously depending on the difference in viscosity between the blood and gas. Alternately, the application of suction device 32 may be regulated in response to a signal from sensor 42. When sensor 42 detects the presence of accumulated gas 50, the signal from sensor 42 causes suction device 32 to operate to remove gas 50. A means for regulating suction device 32 that is coupled to sensor 42 may include circuitry to detect the signal from sensor 42. The circuitry is coupled to a valve or similar device for intermittent application of suction device 32. Though not shown in every Figure, sensor 42 may also be utilized in any embodiment of the present invention.

Figure 3:
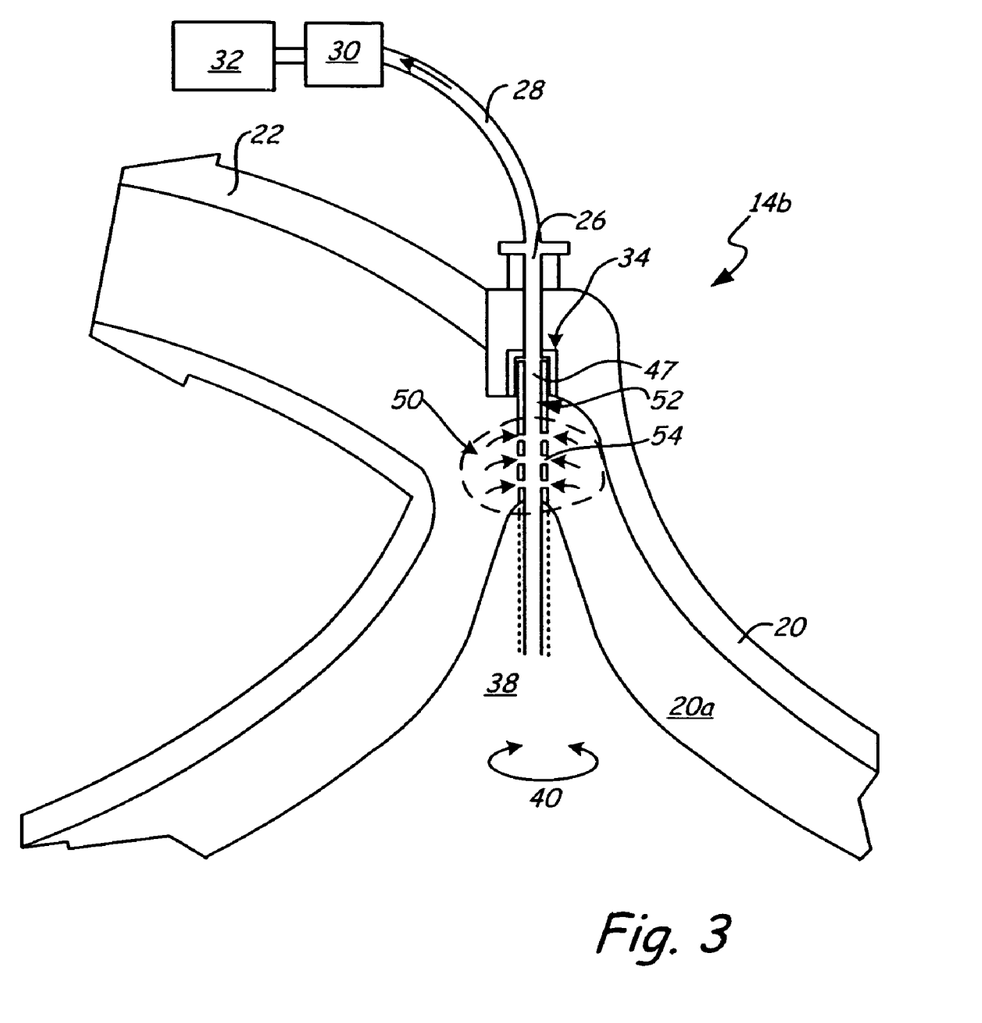
FIG. 3 is a cross-sectional view of a second embodiment of the present invention.

FIG. 3 is a second embodiment showing pump 14b. Pump 14b includes pump housing 20, pump chamber 20a, inlet 22, suction port 26, suction tubing 28, bearing 34, impeller 38, axis of rotation 40, vent 47, hollow rotating shaft 52, and vent inlets 54. FIG. 3 also shows reservoir 30, suction device 32, and accumulated gas 50.

Here, vent 47 extends through shaft 52 such that vent 47 is in fluid communication with suction tubing 28. Suction port 26 is used to connect suction tubing 28 to housing 20. Suction port 26 may be, for example, a luer connector.

Vent inlets 54 are located along shaft 52 such that vent 47 is in fluid communication with pump chamber 20a. Vent inlets 54 are placed in a location where accumulated gas 50 accumulates along shaft 52. Though shown having multiple vents, one or more vents may be utilized with pump 14b.

In operation, as accumulated gas 50 accumulates, suction device 32 draws accumulated gas 50 through vent inlets 54, vent 47, and suction tubing 28 and out of chamber 20a. Suction device 32 may be regulated by any of the means described above.

Figure 4:
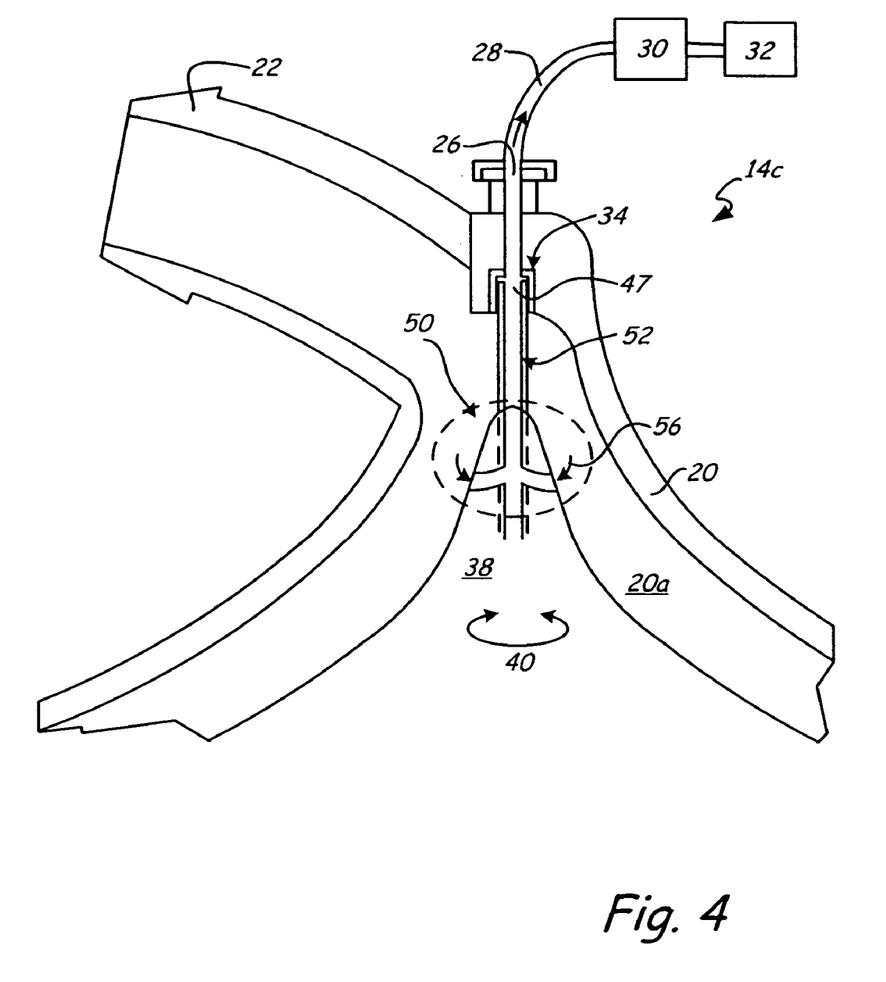
FIG. 4 is a cross-sectional view of a third embodiment of the present invention.

FIG. 4 is a third embodiment showing pump 14c. Pump 14c includes pump housing 20, pump chamber 20a, inlet 22, suction port 26, suction tubing 28, bearing 34, impeller 38, axis of rotation 40, vent 47, hollow rotating shaft 52, and vent inlets 56. FIG. 4 also shows reservoir 30, suction device 32, and accumulated gas 50.

In this embodiment, vent inlets 56 are located on impeller 38. Thus, suction tubing 28 is in fluid communication with vent 47, which is in fluid communication with pump chamber 20a via vent inlets 56. Vent inlets 56 are placed at a location where accumulated gas 50 accumulates. Again, one or more vent inlets may be used in pump 14c.

In operation, as accumulated gas 50 accumulates within pump chamber 20a, suction device 32 draws gas 50 through vent inlets 56, vent 47, and suction tubing 28 and out of chamber 20a. Again, suction device 32 may be regulated by any of a number of ways including those described previously.

Figure 5:
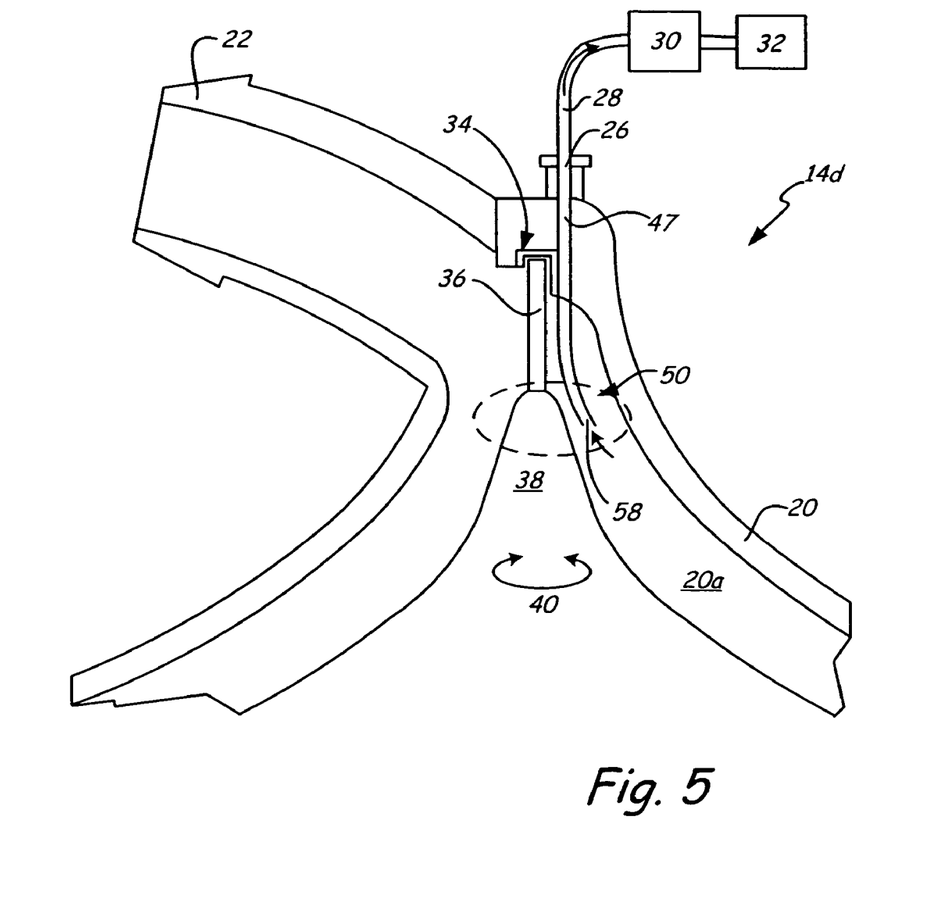
FIG. 5 is a cross-sectional view of a fourth embodiment of the present invention.

FIG. 5 is a fourth embodiment showing pump 14d. Pump 14d includes pump housing 20, pump chamber 20a, inlet 22, suction port 26, suction tubing 28, bearing 34, shaft 36, impeller 38, axis of rotation 40, vent 47, and vent inlet 58. FIG. 5 also shows reservoir 30, suction device 32, and accumulated gas 50.

Here, vent 47 includes tubing that extends from beyond suction port 26 into pump chamber 20a. Vent inlet 58 is the opening of vent 47. Vent inlet 58 is placed near shaft 36 and/or impeller 38 where accumulated gas 50 accumulates.

In operation, accumulated gas 50 is drawn through vent inlet 58, vent 47, and suction tubing 28 out of chamber 20a by suction device 32. In this embodiment, suction device 32 may be regulated by any of the means described previously.

Figure 6:
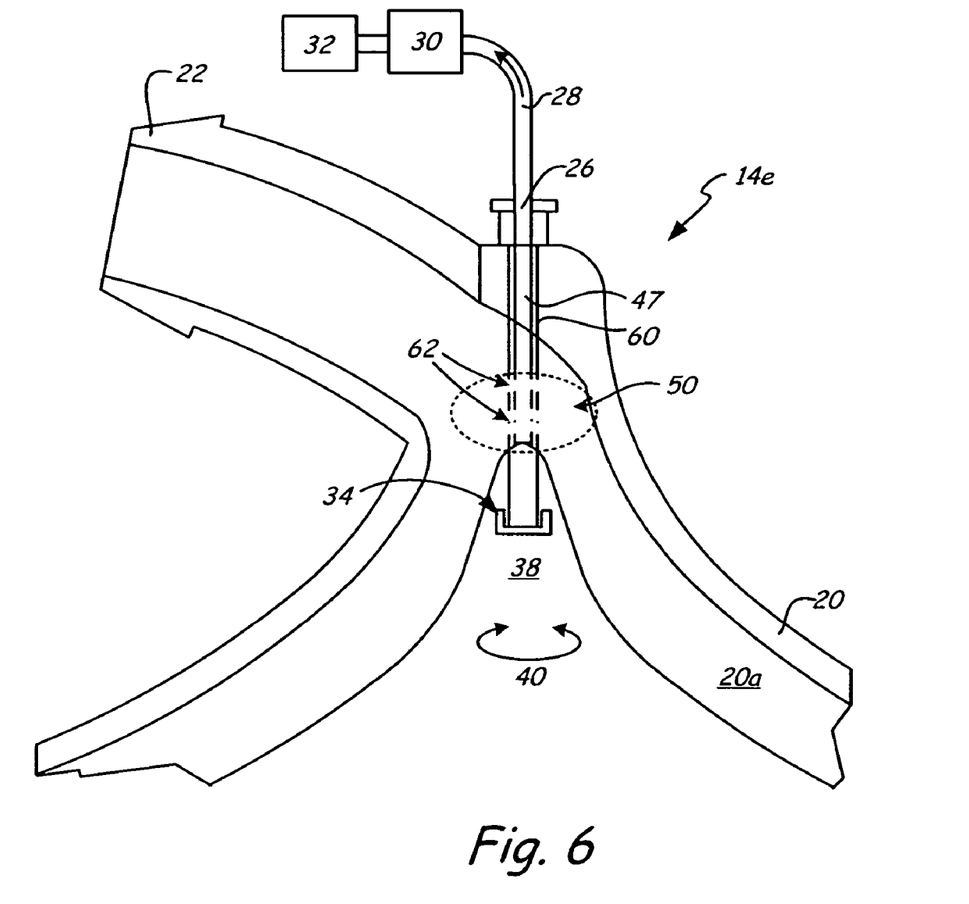
FIG. 6 is a cross-sectional view of a fifth embodiment of the present invention.

FIG. 6 is a fifth embodiment showing pump 14e. Pump 14e includes pump housing 20, pump chamber 20a, inlet 22, suction port 26, suction tubing 28, bearing 34, impeller 38, axis of rotation 40, vent 47, stationary hollow shaft 60, and vent inlets 62. FIG. 6 also shows reservoir 30, suction device 32, and accumulated gas 50.

Shaft 60 does not rotate but supports impeller 38. Vent 47 is within shaft 60. One or more of vent inlets 62 are located along shaft 60 and allow fluid communication between vent 47 and pump chamber 20a.

In operation, as gas 50 accumulates, suction device 32 draws gas 50 through vent inlets 62, through vent 47, through suction tubing 28 and out of pump chamber 20a. Regulation of suction device 32 may be performed as described previously.

Figure 7:
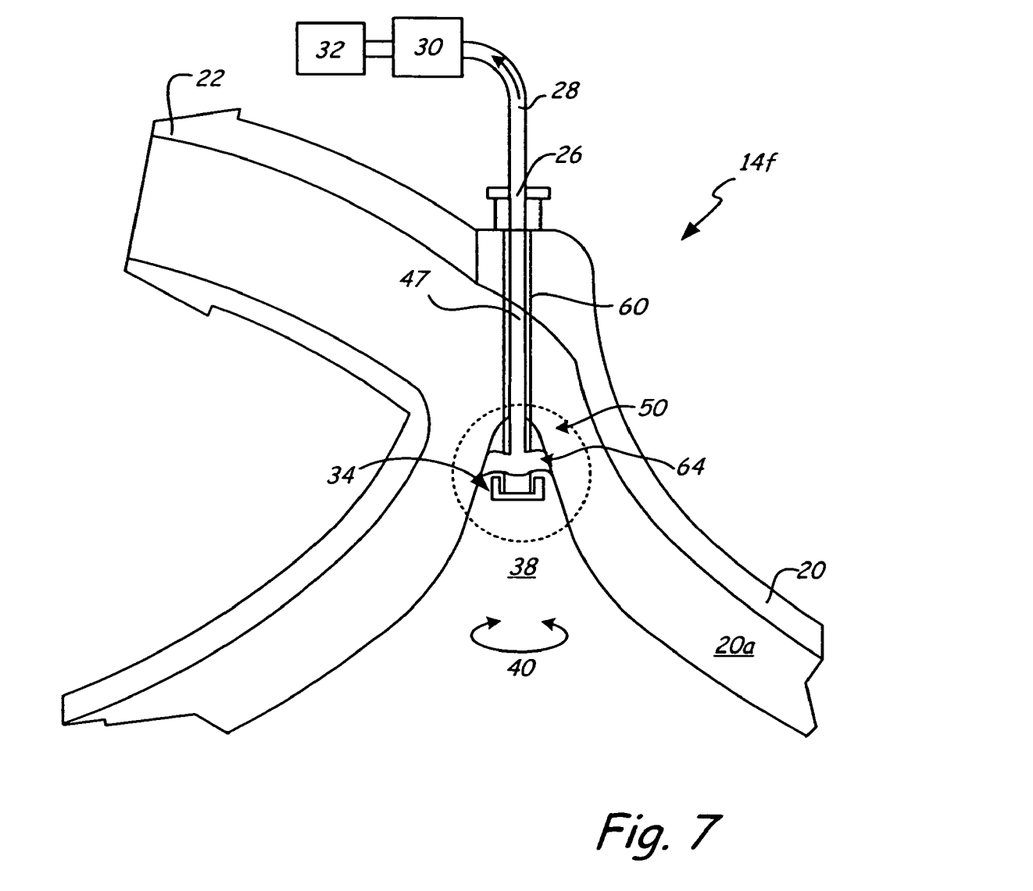
FIG. 7 is a cross-sectional view of a sixth embodiment of the present invention.

FIG. 7 is a sixth embodiment showing pump 14f. Pump 14f includes pump housing 20, pump chamber 20a, inlet 22, suction port 26, suction tubing 28, bearing 34, impeller 38, axis of rotation 40, vent 47, stationary hollow shaft 60, and vent inlets 64. FIG. 7 also shows reservoir 30, suction device 32, and accumulated gas 50.

Here, vent inlets 64 are positioned along impeller 38, which allows fluid communication between vent 47 and pump chamber 20a. When in operation, suction device 32 draws gas 50 through vent inlets 64, vent 47, and suction tubing 28, which removes gas 50 from pump chamber 20a.

With the present invention, gas removal from a closed system is accomplished as a byproduct of the centrifugal pump's characteristic of temporarily concentrating small amounts of gas along the axis of rotation of the shaft and impeller at a position with minimum diameter rather than passing it through with the fluid. By removing the accumulated gas through a vent that is located in the area where the gas accumulates, the risk of complications associated with gas entrained in a closed system are reduced.

Although the present invention has been described with reference to preferred embodiments, workers skilled in the art will recognize that changes may be made in form and detail without departing from the spirit and scope of the invention.

The invention claimed is:

1. A centrifugal pump for pumping biological fluids such as blood, the pump comprising:
   a housing defining a pump chamber;
   a shaft within the pump chamber, the shaft defining an axis of rotation;
   an impeller within the pump chamber, the impeller rotatable about the axis of rotation;
   a fluid inlet in communication with the chamber that is external to the impeller;
   a fluid outlet in communication with the chamber; and
   means for removing gas from a position along the axis of rotation where the gas tends to accumulate, wherein the means for removing gas is positioned near the fluid inlet;
   and wherein the means for removing gas further comprises:
   a shroud surrounding a portion of the shaft, the shroud forming a collection space to collect the gas;
   a vent in communication with the collection space;
   suction tubing in communication with the vent; and
   a suction device coupled to the suction tubing to remove the gas from the collection space.

2. The centrifugal pump of claim 1 wherein the position along the axis of rotation has a minimum diameter.

3. The centrifugal pump of claim 1 and further comprising:
   a reservoir in fluid communication with the suction tubing and suction device.

4. The centrifugal pump of claim 3 wherein the reservoir is a cardiometry reservoir.

5. A centrifugal pump for pumping biological fluids such as blood, the pump comprising:
   a housing defining a pump chamber;
   a shaft within the pump chamber, the shaft defining an axis of rotation;
   an impeller within the pump chamber, the impeller rotatable about the axis of rotation;
   a fluid inlet in communication with the chamber that is external to the impeller;
   a fluid outlet in communication with the chamber;
   means for removing gas from a position along the axis of rotation where the gas tends to accumulate, wherein the means for removing gas is positioned near the fluid inlet; and
   wherein the means for removing gas further comprises:
   a vent within the shaft;
   at least one vent inlet in the shaft for communicating between the pump chamber and the vent; and
   suction tubing in communication with the vent and connectable to a suction device.

6. The centrifugal pump of claim 5 wherein the shaft is a rotating shaft.

7. A centrifugal pump for pumping biological fluids such as blood, the pump comprising:
   a housing defining a pump chamber;
   a shaft within the pump chamber, the shaft defining an axis of rotation;
   an impeller within the pump chamber, the impeller rotatable about the axis of rotation;
   a fluid inlet in communication with the chamber that is external to the impeller;
   a fluid outlet in communication with the chamber; and
   means for removing gas from a position along the axis of rotation where the gas tends to accumulate, wherein the means for removing gas is positioned near the fluid inlet; and
   wherein the means for removing gas further comprises:
   a vent within the shaft;
   at least one vent inlet in the impeller that communicates between the pump chamber and the vent; and
   suction tubing in communication with the vent and connectable to a suction device.

8. The centrifugal pump of claim 7 wherein the shaft is a rotating shaft.

9. A centrifugal pump that is used for pumping biological fluids such as blood and removes accumulated gas from within the pump, the centrifugal pump comprising:
   a pump chamber;
   an impeller within the pump chamber, the impeller having a minimum diameter and a maximum diameter;
   a fluid inlet in communication with the pump chamber that is external to the impeller, wherein the fluid inlet is positioned near the minimum diameter of the impeller;
   a fluid outlet in communication with the pump chamber, wherein the fluid outlet is positioned near the maximum diameter of the impeller;
   a vent inlet positioned near an axis of rotation of the impeller where the minimum diameter is located;
   a vent in fluid communication with the vent inlet; and
   suction tubing in fluid communication with the vent;
   wherein the vent inlet is on a shaft and the vent is within the shaft, the vent inlet providing fluid communication between the pump chamber and the vent.

10. The centrifugal pump of claim 9 and further comprising a suction device in fluid communication with the suction tubing.

11. The centrifugal pump of claim 9 wherein the shaft rotates with the impeller.

12. A centrifugal pump that is used for pumping biological fluids such as blood and removes accumulated gas from within the pump, the centrifugal pump comprising:
   a pump chamber;
   an impeller within the pump chamber, the impeller having a minimum diameter and a maximum diameter;
   a fluid inlet in communication with the pump chamber that is external to the impeller, wherein the fluid inlet is positioned near the minimum diameter of the impeller;
   a fluid outlet in communication with the pump chamber, wherein the fluid outlet is positioned near the maximum diameter of the impeller;

a vent inlet positioned near an axis of rotation of the impeller where the minimum diameter is located;
a vent in fluid communication with the vent inlet; and
suction tubing in fluid communication with the vent;
wherein the vent inlet is on the impeller inside the pump chamber, the vent is within a shaft inside the pump chamber, and the vent inlet provides fluid communication between the vent and the pump chamber.

13. The centrifugal pump of claim 12 wherein the shaft rotates with the impeller.

14. A centrifugal pump that is used for pumping biological fluids such as blood and removes accumulated gas from within the pump, the centrifugal pump comprising:
a pump chamber:
an impeller within the pump chamber, the impeller having a minimum diameter and a maximum diameter;
a fluid inlet in communication with the pump chamber that is external to the impeller, wherein the fluid inlet is positioned near the minimum diameter of the impeller;
a fluid outlet in communication with the pump chamber, wherein the fluid outlet is positioned near the maximum diameter of the impeller;
a vent inlet positioned near an axis of rotation of the impeller where the minimum diameter is located;
a vent in fluid communication with the vent inlet;
suction tubing in fluid communication with the vent;
a shroud forming a collection space to collect the gas; and
wherein the vent inlet provides fluid communication between the collection space and the vent.

15. A centrifugal pump for pumping biological fluids such as blood, the pump comprising:
a housing defining a pump chamber;
a fluid inlet in communication with the chamber;
a fluid outlet in communication with the chamber;
a shaft within the pump chamber, the shaft defining an axis of rotation, wherein the shaft is a stationary shaft;
an impeller within the pump chamber, the impeller rotatable about the axis of rotation; and
means for removing gas from a position along the axis of rotation where the gas tends to accumulate, wherein the means for removing gas is positioned near the fluid inlet, and wherein the means for removing gas comprises:
a vent within the shaft; and
at least one vent inlet in the shaft for communicating between the pump chamber and the vent; and
suction tubing in communication with the vent and connectable to a suction device.

16. A centrifugal pump that is used for pumping biological fluids such as blood and removes accumulated gas from within the pump, the centrifugal pump comprising:
a pump chamber;
an impeller within the pump chamber;
a vent inlet positioned near an axis of rotation of the impeller where a minimum diameter is located;
a vent in fluid communication with the vent inlet; and
suction tubing in fluid communication with the vent;
wherein the vent inlet is on a stationary shaft and the vent is within the shaft, the vent inlet providing fluid communication between the pump chamber and the vent.

17. A centrifugal pump that is used for pumping biological fluids such as blood and removes accumulated gas from within the pump, the centrifugal pump comprising:
a pump chamber;
an impeller within the pump chamber;
a vent inlet positioned near an axis of rotation of the impeller where a minimum diameter is located;
a vent in fluid communication with the vent inlet;
suction tubing in fluid communication with the vent; and
wherein the vent inlet is on the impeller inside the pump chamber, the vent is within a stationary shaft inside the pump chamber, and the vent inlet provides fluid communication between the vent and the pump chamber.

* * * * *